(12) United States Patent
Zhu et al.

(10) Patent No.: US 6,596,524 B2
(45) Date of Patent: Jul. 22, 2003

(54) **METHOD FOR CLONING AND EXPRESSION OF *BSMAI* RESTRICTION ENDONUCLEASE AND *BSMAI* METHYLASE IN *E. COLI***

(75) Inventors: Zhenyu Zhu, Beverly, MA (US); Jing Zhou, Beverly, MA (US); Shuang-yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 55 days.

(21) Appl. No.: 09/957,005

(22) Filed: Sep. 20, 2001

(65) Prior Publication Data

US 2003/0104388 A1 Jun. 5, 2003

(51) Int. Cl.[7] .............................. C12N 9/22; C12N 15/55
(52) U.S. Cl. ............... 435/199; 435/320.1; 435/252.33; 536/23.2
(58) Field of Search .............................. 435/199, 320.1, 435/252.33; 536/23.2

(56) References Cited

U.S. PATENT DOCUMENTS 5,200,333 A   4/1993   Wilson ..................... 435/172.3

OTHER PUBLICATIONS

Kong, H., et al. (1990) Nucl. Acids Res. 18(3), 686.*
Roberts and Macelis, Nucl. Acids Res. 27: 312–313, (1999).
Kosykh et al., Mol. Gen. Genet. 178: 717–719, (1980).
Mann et al., Gene 3: 97–112, (1978).
Walder et al., Proc. Nat. Acad, Sci. 78: 1503–1507, (1981).
Bougeleret et al., Nucl. Acids Res. 12: 3659–3676, (1984).
Gingeras and Brooks, Proc. Natl. Acad. Sci. USA 80: 402–406, (1983).
Theriault and Roy, Gene 19: 355–359 (1982).
Blumenthal et al., J. Bacteriol. 164: 501–509 (1985).
Wayne et al., Gene 202: 83–88, (1997).
Kiss et al., Nucl. Acids Res. 13: 6403–6421, (1985).
Szomolanyi et al., Gene 10: 219–225, (1980).
Janulaitis et al., Gene 20: 197–204, (1982).
Kiss and Baldauf, Gene 21: 111–119, (1983).
Walder et al., J. Biol. Chem. 258: 1235–1241, (1983).
Fomenkov et al., Nucl. Acids Res. 22: 2399–2403, (1994).
Malone et al., J. Mol. Biol. 253: 618–632, (1995).
New England Biolabs' Catalog, 2000–01, p. 220.

* cited by examiner

*Primary Examiner*—Charles L. Patterson, Jr.
(74) *Attorney, Agent, or Firm*—Gregory D. Williams

(57) ABSTRACT

The present invention relates to recombinant DNA which encodes the BsmAI restriction endonuclease as well as BsmAI methylase, expression of BsmAI restriction endonuclease and BsmAI methylase in *E. coli* cells containing the recombinant DNA, and purification of BsmAI endonuclease to near homogeneity.

6 Claims, 9 Drawing Sheets

FIG. 2A

```
     ATGAATGGAGGTGCTTGTGTGAAAGAAAACACAGAAATTAATATAGATATTAAAAAAGCA
  1  ------------+---------+---------+---------+---------+---------+  60
      M  N  G  G  A  C  V  K  E  N  T  E  I  N  I  D  I  K  K  A
     GCATTATGGGATACGATTAGGAATAAAAGCCAATTCCTTGAAACTCAAATGGATCCTTTG
 61  ------------+---------+---------+---------+---------+---------+ 120
      A  L  W  D  T  I  R  N  K  S  Q  F  L  E  T  Q  M  D  P  L
     GAGAGAAAAAGAACAGGTAGCTATTTTACTGCACTGGAATTAACAGATGTTATGATGCAG
121  ------------+---------+---------+---------+---------+---------+ 180
      E  R  K  R  T  G  S  Y  F  T  A  L  E  L  T  D  V  M  M  Q
     GAGTTGGTTTCGTACATACTAAAAAGCGATAAAGATATTACAGAATTAAAGTTTTTAGAA
181  ------------+---------+---------+---------+---------+---------+ 240
      E  L  V  S  Y  I  L  K  S  D  K  D  I  T  E  L  K  F  L  E
     CCTTGTGTTGGAACGGGAAACTTTGTCTTTTCATATCTAAAAGAAATAAGCAAATTGCAG
241  ------------+---------+---------+---------+---------+---------+ 300
      P  C  V  G  T  G  N  F  V  F  S  Y  L  K  E  I  S  K  L  Q
     TTGCACAAGGAGCAGATCGAAACTCTGATTAACAATATATATGTTGCGGATATTAACCAA
301  ------------+---------+---------+---------+---------+---------+ 360
      L  H  K  E  Q  I  E  T  L  I  N  N  I  Y  V  A  D  I  N  Q
     ACGGCTTTGTTAGAATATAAAAAGTTGCTTTCTAAGTTTGCAAAATTATATTTTGATATT
361  ------------+---------+---------+---------+---------+---------+ 420
      T  A  L  L  E  Y  K  K  L  L  S  K  F  A  K  L  Y  F  D  I
     GATTTATCTGAAGAATACTTTAATTCTCACATTGGATCAGCCTTATTGATTGATGTGGCA
421  ------------+---------+---------+---------+---------+---------+ 480
      D  L  S  E  E  Y  F  N  S  H  I  G  S  A  L  L  I  D  V  A
     GCAGAACAGCcTGAATATATAAAAATAACAGATGTCTTTCCAGATGAAGTAGTTAAAGAA
481  ------------+---------+---------+---------+---------+---------+ 540
      A  E  Q  P  E  Y  I  K  I  T  D  V  F  P  D  E  V  V  K  E
     GGTTTTGATATCGTTGTCACAAATCCACCATATAAAAATCTTAAGGCAGAAAAAGGACAG
541  ------------+---------+---------+---------+---------+---------+ 600
      G  F  D  I  V  V  T  N  P  P  Y  K  N  L  K  A  E  K  G  Q
     TATTCTAATGACTTAGAATATGAAATAGATAGAGCTAGATATGCTGAAATAAAAAAAATG
601  ------------+---------+---------+---------+---------+---------+ 660
      Y  S  N  D  L  E  Y  E  I  D  R  A  R  Y  A  E  I  K  K  M
     GTAAAACGAATATTTAACTATTCAACCGATGGTGTACTCAACCTATATAAACTTTTTGTT
661  ------------+---------+---------+---------+---------+---------+ 720
      V  K  R  I  F  N  Y  S  T  D  G  V  L  N  L  Y  K  L  F  V
     GAAGAGATTATAGATAAGTACGCTAACCCTAATGGAtTTGTAAGTTTACTTATTCCATCA
721  ------------+---------+---------+---------+---------+---------+ 780
      E  E  I  I  D  K  Y  A  N  P  N  G  F  V  S  L  L  I  P  S
     TCTATTCTTACAGATAAAACTTGTACAAAATTAAGAACACATATGCTTGTAGATAGCAAT
781  ------------+---------+---------+---------+---------+---------+ 840
      S  I  L  T  D  K  T  C  T  K  L  R  T  H  M  L  V  D  S  N
```

FIG. 2B

```
     ATCTTATCAATAAAGATGATAAACGAAGGTAGTGGATACATTGATGCTCAGCAGGCTTTG
841  ------------+---------+---------+---------+---------+---------+  900
      I  L  S  I  K  M  I  N  E  G  S  G  Y  I  D  A  Q  Q  A  L
     AGTGCAATATTAATTCAAAAAGGTAAAAGGACAGAATCTATTAAGGTAACAAAAGATTAT
901  ------------+---------+---------+---------+---------+---------+  960
      S  A  I  L  I  Q  K  G  K  R  T  E  S  I  K  V  T  K  D  Y
     AGCAATAACCCTAATCAGATTACAGATATTAACATGGAAGACATTCTTAATGAAAACACA
961  ------------+---------+---------+---------+---------+---------+  1020
      S  N  N  P  N  Q  I  T  D  I  N  M  E  D  I  L  N  E  N  T
     GGAAATGCTATATTTGCTATTAATAATCATGAATATTTCATTCTTAAACAGCTAAGAAAG
1021 ------------+---------+---------+---------+---------+---------+  1080
      G  N  A  I  F  A  I  N  N  H  E  Y  F  I  L  K  Q  L  R  K
     TTTCCTGTCGTCAAAGATTTAGATTTTATTATTAATCTTCGTGGAGAATTAGATTTAACA
1081 ------------+---------+---------+---------+---------+---------+  1140
      F  P  V  V  K  D  L  D  F  I  I  N  L  R  G  E  L  D  L  T
     GCAAATAAGGATTCTATTGTAAATATCGATACAGGTTATCCGCTCTTAAGAGGAAGAAAT
1141 ------------+---------+---------+---------+---------+---------+  1200
      A  N  K  D  S  I  V  N  I  D  T  G  Y  P  L  L  R  G  R  N
     ATAGGTTATTATGAGATTTTGGATACTTGTAGTGGGGAGTTTGTATCGAAGGATTTTATA
1201 ------------+---------+---------+---------+---------+---------+  1260
      I  G  Y  Y  E  I  L  D  T  C  S  G  E  F  V  S  K  D  F  I
     GAAAACAGCAAGAAATCACGATATATTAAAGAAAAGAGAATTGTCTGTCAGCAAGTTGTT
1261 ------------+---------+---------+---------+---------+---------+  1320
      E  N  S  K  K  S  R  Y  I  K  E  K  R  I  V  C  Q  Q  V  V
     AATATGAAGAAAGAGAGAAGGGTAACATTTGCTTTAGTAGAAGAAAATTATGTTTTAGGA
1321 ------------+---------+---------+---------+---------+---------+  1380
      N  M  K  K  E  R  R  V  T  F  A  L  V  E  E  N  Y  V  L  G
     AACTCATGCAATTTTATATCTGTAATGGATAATGATTATAACATTGATTTATATGCTATA
1381 ------------+---------+---------+---------+---------+---------+  1440
      N  S  C  N  F  I  S  V  M  D  N  D  Y  N  I  D  L  Y  A  I
     CTTGGACTATTCAACACTTCAATTATTAATTGGTTATTTAAGTTAACAAGTAGCAATAAT
1441 ------------+---------+---------+---------+---------+---------+  1500
      L  G  L  F  N  T  S  I  I  N  W  L  F  K  L  T  S  S  N  N
     CATGTTAATAACTATGAGATTGATTGTTTTCCCGTTCCAATTGGATCTCCTTATTTAAAT
1501 ------------+---------+---------+---------+---------+---------+  1560
      H  V  N  N  Y  E  I  D  C  F  P  V  P  I  G  S  P  Y  L  N
     AAAATTAGTAACCTGGTAAAAAAATATCTTAGTAATAAAGACTCATCGTTGCTAGAAAAA
1561 ------------+---------+---------+---------+---------+---------+  1620
      K  I  S  N  L  V  K  K  Y  L  S  N  K  D  S  S  L  L  E  K
     ATAGAGGAATATGCGTATATAGCATATGGAATCAGAGAAGCAAAAGAGGATAATGAGGAT
1621 ------------+---------+---------+---------+---------+---------+  1680
      I  E  E  Y  A  Y  I  A  Y  G  I  R  E  A  K  E  D  N  E  D
```

FIG. 2C

```
      AAAGATGATATAGCTAATCTAAAAGAAACTAACGATATTATAAAAAAATATTATTCAGCA
1681  ------------------------------------------------------------  1740
       K  D  D  I  A  N  L  K  E  T  N  D  I  I  K  K  Y  Y  S  A
      ATAAAACATGTTCTACCAAGTATAACACTGGAAGATTCAGTCAGTATCCTTGAGGGGCAA
1741  ------------------------------------------------------------  1800
       I  K  H  V  L  P  S  I  T  L  E  D  S  V  S  I  L  E  G  Q
      TCTTCAATAGAATCCTTTATACTGCAATCTGGAGTTGAATTAGATAAATACACACGTAAT
1801  ------------------------------------------------------------  1860
       S  S  I  E  S  F  I  L  Q  S  G  V  E  L  D  K  Y  T  R  N
      ATAGTTTTGGGAATTACTGATAAATATATGAAAATTAAAAAAGGAGAAATACTTAATCAT
1861  ------------------------------------------------------------  1920
       I  V  L  G  I  T  D  K  Y  M  K  I  K  K  G  E  I  L  N  H
      ACTACTTTCAAATTAAGTGACTTAGATTTGGAAATGATACGCTCTGTTCCACCCGGAGGC
1921  ------------------------------------------------------------  1980
       T  T  F  K  L  S  D  L  D  L  E  M  I  R  S  V  P  P  G  G
      AACTGGAAGGACATACCAATTGAAACGGTAAAAAAATTTAAGAGATTAATGAGAATTACA
1981  ------------------------------------------------------------  2040
       N  W  K  D  I  P  I  E  T  V  K  K  F  K  R  L  M  R  I  T
      GAAACAGGTGGGCGAACAACATTATATGGTCGAATTGACTATGATAAGCCAAGTTACACG
2041  ------------------------------------------------------------  2100
       E  T  G  G  R  T  T  L  Y  G  R  I  D  Y  D  K  P  S  Y  T
      ATTACGACTTATTTTAATAGGCCTGGAAATGGAACCTATGTGCATCCTGTTCATGATAGA
2101  ------------------------------------------------------------  2160
       I  T  T  Y  F  N  R  P  G  N  G  T  Y  V  H  P  V  H  D  R
      GTTCTTTCTGTTAGGGAGGCTGCACGATTCCAATGTTTTAAGGATGATTATTATTTTTAT
2161  ------------------------------------------------------------  2220
       V  L  S  V  R  E  A  A  R  F  Q  C  F  K  D  D  Y  Y  F  Y
      GGAAACAAGACACAAATGCTTAAACAGGTTGGAAATGCTGTGCCAACAATTCTAGCTTAT
2221  ------------------------------------------------------------  2280
       G  N  K  T  Q  M  L  K  Q  V  G  N  A  V  P  T  I  L  A  Y
      CAAATTGCAAAGAAGATAGTTGATAAAACAGGTTGTAGAAAGTCAATAGATCTCTTCTGT
2281  ------------------------------------------------------------  2340
       Q  I  A  K  K  I  V  D  K  T  G  C  R  K  S  I  D  L  F  C
      GGGGCAGGTGGATTAACTGCAGGATTTAAAGAGGCTGGAATTCAATCAGTTTTATGTAAC
2341  ------------------------------------------------------------  2400
       G  A  G  G  L  T  A  G  F  K  E  A  G  I  Q  S  V  L  C  N
      GATATCGAAGAAAGTGCATGTATAACTTTGAAAATTAATAACCCTGAGATTAAAGTTTTA
2401  ------------------------------------------------------------  2460
       D  I  E  E  S  A  C  I  T  L  K  I  N  N  P  E  I  K  V  L
      TGTGGTGATATTTCTCAACATGAAACAAAGGAGCATATTGTTAATGTTGCAATAAATGAA
2461  ------------------------------------------------------------  2520
       C  G  D  I  S  Q  H  E  T  K  E  H  I  V  N  V  A  I  N  E
      GATGTTGATATTATTTGTGGAGGTCCACCTTGTCAAGGCTTTTCAATGGCGGGATTGAGA
2521  ------------------------------------------------------------  2580
       D  V  D  I  I  C  G  G  P  P  C  Q  G  F  S  M  A  G  L  R
```

FIG. 2D

```
     TTAACAGATGACCCAAGAAATCAGCTTTTTAAGGAATTCATTGAAATAGTAAGTCGAGTA
2581 ------------+---------+---------+---------+---------+---------+ 2640
      L  T  D  D  P  R  N  Q  L  F  K  E  F  I  E  I  V  S  R  V
     AAGCCTAAAGTAATTGTATTTGAAAATGTTGAAGGGATTCTTAGTTTTCAGAGTGGAAAG
2641 ------------+---------+---------+---------+---------+---------+ 2700
      K  P  K  V  I  V  F  E  N  V  E  G  I  L  S  F  Q  S  G  K
     GTATATCGTGCGATATTAGAGATGTTTTCAGAAATAGGATATTTTACTGAAGGACGAACT
2701 ------------+---------+---------+---------+---------+---------+ 2760
      V  Y  R  A  I  L  E  M  F  S  E  I  G  Y  F  T  E  G  R  T
     TTAATGTCAAGCGACTATGCCGTTCCTCAAAAACGAAAGAGAGTTTTTATTATCTGTACT
2761 ------------+---------+---------+---------+---------+---------+ 2820
      L  M  S  S  D  Y  A  V  P  Q  K  R  K  R  V  F  I  I  C  T
     CGTGATGATATGGACGTAAAACCGGCAGATTTATTTCCAACTCCTATTACAGAAGAGCCC
2821 ------------+---------+---------+---------+---------+---------+ 2880
      R  D  D  M  D  V  K  P  A  D  L  F  P  T  P  I  T  E  E  P
     GAATGTCAAATTACAGCCAGGGATACTATCAAAGATTTAGAAAACATCCAGTGTGATGAA
2881 ------------+---------+---------+---------+---------+---------+ 2940
      E  C  Q  I  T  A  R  D  T  I  K  D  L  E  N  I  Q  C  D  E
     AAAGCTTGTTATGTTAAAGTGGAACATGAATCTGATATCCTGAAGGTTTTTAAAGGGAAA
2941 ------------+---------+---------+---------+---------+---------+ 3000
      K  A  C  Y  V  K  V  E  H  E  S  D  I  L  K  V  F  K  G  K
     ATGACGTACCAAGAAATATATTAG
3001 ------------+---------+----  3024
      M  T  Y  Q  E  I  Y  *
```

FIG. 3A

```
      ATGGCAAGAGAAGAAAGAGAATGGCATCCTAAATTTATTGAATATATGGATTTCATTATT
  1   ------------+---------+---------+---------+---------+---------+  60
       M  A  R  E  E  R  E  W  H  P  K  F  I  E  Y  M  D  F  I  I
      CAACATCCAAATTACAAAGGTTTACCAATAACTAAAAAATCTGATGGATCTTGGTCTTGG
 61   ------------+---------+---------+---------+---------+---------+ 120
       Q  H  P  N  Y  K  G  L  P  I  T  K  K  S  D  G  S  W  S  W
      TTTGGTACAAAGAAAACACAAATTGGAAAAGCAAGGATAGCTTGGTGTGAAAATAAAGCT
121   ------------+---------+---------+---------+---------+---------+ 180
       F  G  T  K  K  T  Q  I  G  K  A  R  I  A  W  C  E  N  K  A
      AAAGAATTAGGATTTCCAATTGAGCCAGGCGTTTATGCGAATGTTATGCgTGAGATTCAT
181   ------------+---------+---------+---------+---------+---------+ 240
         K  E  L  G  F  P  I  E  P  G  V  Y  A  N  V  M  R  E  I  H
      CCAACCAAATGGAAAGTATGTCAAACCTGTGGCCATTCAATGTCAATTTATTATCACTAT
241   ------------+---------+---------+---------+---------+---------+ 300
       P  T  K  W  K  V  C  Q  T  C  G  H  S  M  S  I  Y  Y  H  Y
      CCAAGTGCTAATTTTCTTAAGGCTCTAAAAAAAGAGTTCGGTGTTGAATATACTGAAGTT
301   ------------+---------+---------+---------+---------+---------+ 360
       P  S  A  N  F  L  K  A  L  K  K  E  F  G  V  E  Y  T  E  V
      GACCACATCGCCGACATTTGGGATGATTTGCTTAGCCGGGGGTTTTCAAACAATAAAATA
361   ------------+---------+---------+---------+---------+---------+ 420
       D  H  I  A  D  I  W  D  D  L  L  S  R  G  F  S  N  N  K  I
      GCTTCATTTCTTATAAAAAAGGGTGAATTAGATTTAAACGCTAAAACCTCAAGTAAAGAT
421   ------------+---------+---------+---------+---------+---------+ 480
       A  S  F  L  I  K  K  G  E  L  D  L  N  A  K  T  S  S  K  D
      GAAGTTATTTATGAACTTGAATCAGTTTGTAGAAACAAAGGGAAAAAAATATTGAGCCCT
481   ------------+---------+---------+---------+---------+---------+ 540
       E  V  I  Y  E  L  E  S  V  C  R  N  K  G  K  K  I  L  S  P
      GGAGCCATGTCAAACTTTCCAGATCGATTTGATGGATTCCATACCTATAACCGTTGCTGC
541   ------------+---------+---------+---------+---------+---------+ 600
       G  A  M  S  N  F  P  D  R  F  D  G  F  H  T  Y  N  R  C  C
      AGAGCATCGCAAGATAAGGGACGTTCAAAAGAAAACCTAAAATCGTATACAAAAGATAGA
601   ------------+---------+---------+---------+---------+---------+ 660
       R  A  S  Q  D  K  G  R  S  K  E  N  L  K  S  Y  T  K  D  R
      CGTGCATATGAATATTGGAGCGATGGAAATATTCATGCGGCCAACCAATTTATGGGGAGC
661   ------------+---------+---------+---------+---------+---------+ 720
       R  A  Y  E  Y  W  S  D  G  N  I  H  A  A  N  Q  F  M  G  S
      CCATTCTTTAATAATATTTCAGCTGATCATATTGGTCCTATTTCATTAGGGTTTGTACAT
721   ------------+---------+---------+---------+---------+---------+ 780
       P  F  F  N  N  I  S  A  D  H  I  G  P  I  S  L  G  F  V  H
      GATCCAAGATATTTACAACCCATGAGTGGCGGTGATAACTCCTCTAAAAGAGACCGCTTA
781   ------------+---------+---------+---------+---------+---------+ 840
       D  P  R  Y  L  Q  P  M  S  G  G  D  N  S  S  K  R  D  R  L
```

FIG. 3B

```
     CAGTTGGATGATATTGAAAAAATTATTGAAACTGAAAAACGCACAAATGTTTATCCTATG
841  ------------------------------------------------------------  900
     Q  L  D  D  I  E  K  I  I  E  T  E  K  R  T  N  V  Y  P  M
     TCATGGTACTCAAAATTAATCTGGGAATACATAAAGAAAAATTACTCTACTCATAAGAGT
901  ------------------------------------------------------------  960
      S  W  Y  S  K  L  I  W  E  Y  I  K  K  N  Y  S  T  H  K  S
     TTAATTTCTGGAGTTTACCGAGATGCTTTAAAGCAGAATATGTCTAATTTTATGTATATA
961  ------------------------------------------------------------ 1020
      L  I  S  G  V  Y  R  D  A  L  K  Q  N  M  S  N  F  M  Y  I
     TTGTGGTATATTCTTGAGCACTGTAACCAAGATGGTGAGCATTTtTTAGAAGAAGCTCTA
1021 ------------------------------------------------------------ 1080
      L  W  Y  I  L  E  H  C  N  Q  D  G  E  H  F  L  E  E  A  L
     TTAAAGCCCAATTATGATTATTTTCAATACTCATATACATTTAATGAATTAGGAGAAATT
1081 ------------------------------------------------------------ 1140
      L  K  P  N  Y  D  Y  F  Q  Y  S  Y  T  F  N  E  L  G  E  I
     GTGAGCATAAACCCACGTCACTTTACTGATAGAAATCAGTATGAAACCGAAAGATACAAA
1141 ------------------------------------------------------------ 1200
      V  S  I  N  P  R  H  F  T  D  R  N  Q  Y  E  T  E  R  Y  K
     CGTATAGCTTTTGAGTCAGTTTATGATTATAATGAAAAAGAAAATAGAAATATAAAAGCA
1201 ------------------------------------------------------------ 1260
      R  I  A  F  E  S  V  Y  D  Y  N  E  K  E  N  R  N  I  K  A
     AACCTCATAGATAATGAGCAAAGAATGTTAAACAAATTGTGCCAGGAAATTTCATCTGGG
1261 ------------------------------------------------------------ 1320
      N  L  I  D  N  E  Q  R  M  L  N  K  L  C  Q  E  I  S  S  G
     GTTCCTGTTGAGCAGTGCAAAAAACTTCTAATAGAATTAATGGAAGTAATTCAAAAAAGA
1321 ------------------------------------------------------------ 1380
      V  P  V  E  Q  C  K  K  L  L  I  E  L  M  E  V  I  Q  K  R
     ATTATATCAACATTATAA
1381 ------------------ 1398
      I  I  S  T  L  *
```

SEQUENCE LISTING

<160> NUMBER OF SEQ ID NOS: 20

<210> SEQ ID NO 1
<211> LENGTH: 5
<212> TYPE: DNA
<213> ORGANISM: Bacillus stearothermophilus

<400> SEQUENCE: 1 gtctc                                                          5

<210> SEQ ID NO 2
<211> LENGTH: 6
<212> TYPE: DNA
<213> ORGANISM: Deinococcus radiophilus

<400> SEQUENCE: 2 tttaaa                                                         6

<210> SEQ ID NO 3
<211> LENGTH: 5

```
<212> TYPE: DNA
<213> ORGANISM: Deinococcus radiophilus
<220> FEATURE:
<223> OTHER INFORMATION: N=G, A, C, or T

<400> SEQUENCE: 3 ggncc                                                                   5

<210> SEQ ID NO 4
<211> LENGTH: 9
<212> TYPE: DNA
<213> ORGANISM: Deinococcus radiophilus
<220> FEATURE:
<223> OTHER INFORMATION: N=G, A, C, or T

<400> SEQUENCE: 4 cacnnngtg                                                               9

<210> SEQ ID NO 5
<211> LENGTH: 6
<212> TYPE: DNA
<213> ORGANISM: Escherichia coli

<400> SEQUENCE: 5 gaattc                                                                  6

<210> SEQ ID NO 6
<211> LENGTH: 5
<212> TYPE: DNA
<213> ORGANISM: Unknown
<220> FEATURE:
<223> OTHER INFORMATION: W=A or T
<223> OTHER INFORMATION: Description of Unknown Organism: Dcm Methylase

<400> SEQUENCE: 6 ccwgg                                                                   5

<210> SEQ ID NO 7
<211> LENGTH: 8
<212> TYPE: DNA
<213> ORGANISM: Neisseria lactamica

<400> SEQUENCE: 7 gcggccgc                                                                8

<210> SEQ ID NO 8
<211> LENGTH: 3024
<212> TYPE: DNA
<213> ORGANISM: Bacillus stearothermophilus A664
<220> FEATURE:
<221> NAME/KEY: CDS
<222> LOCATION: (1)..(3024)

<400> SEQUENCE: 8 atg aat gga ggt gct tgt gtg aaa gaa aac aca gaa att aat ata gat        48
Met Asn Gly Gly Ala Cys Val Lys Glu Asn Thr Glu Ile Asn Ile Asp
 1               5                  10                  15 att aaa aaa gca gca tta tgg gat acg att agg aat aaa agc caa ttc        96
Ile Lys Lys Ala Ala Leu Trp Asp Thr Ile Arg Asn Lys Ser Gln Phe
             20                  25                  30 ctt gaa act caa atg gat cct ttg gag aga aaa aga aca ggt agc tat       144
Leu Glu Thr Gln Met Asp Pro Leu Glu Arg Lys Arg Thr Gly Ser Tyr
         35                  40                  45 ttt act gca ctg gaa tta aca gat gtt atg atg cag gag ttg gtt tcg       192
Phe Thr Ala Leu Glu Leu Thr Asp Val Met Met Gln Glu Leu Val Ser
```

-continued

```
                      50                      55                      60
tac ata cta aaa agc gat aaa gat att aca gaa tta aag ttt tta gaa        240
Tyr Ile Leu Lys Ser Asp Lys Asp Ile Thr Glu Leu Lys Phe Leu Glu
 65                      70                      75                      80 cct tgt gtt gga acg gga aac ttt gtc ttt tca tat cta aaa gaa ata        288
Pro Cys Val Gly Thr Gly Asn Phe Val Phe Ser Tyr Leu Lys Glu Ile
                         85                      90                      95 agc aaa ttg cag ttg cac aag gag cag atc gaa act ctg att aac aat        336
Ser Lys Leu Gln Leu His Lys Glu Gln Ile Glu Thr Leu Ile Asn Asn
                100                     105                     110 ata tat gtt gcg gat att aac caa acg gct ttg tta gaa tat aaa aag        384
Ile Tyr Val Ala Asp Ile Asn Gln Thr Ala Leu Leu Glu Tyr Lys Lys
            115                     120                     125 ttg ctt tct aag ttt gca aaa tta tat ttt gat att gat tta tct gaa        432
Leu Leu Ser Lys Phe Ala Lys Leu Tyr Phe Asp Ile Asp Leu Ser Glu
        130                     135                     140 gaa tac ttt aat tct cac att gga tca gcc tta ttg att gat gtg gca        480
Glu Tyr Phe Asn Ser His Ile Gly Ser Ala Leu Leu Ile Asp Val Ala
145                     150                     155                     160 gca gaa cag cct gaa tat ata aaa ata aca gat gtc ttt cca gat gaa        528
Ala Glu Gln Pro Glu Tyr Ile Lys Ile Thr Asp Val Phe Pro Asp Glu
                    165                     170                     175 gta gtt aaa gaa ggt ttt gat atc gtt gtc aca aat cca cca tat aaa        576
Val Val Lys Glu Gly Phe Asp Ile Val Val Thr Asn Pro Pro Tyr Lys
                180                     185                     190 aat ctt aag gca gaa aaa gga cag tat tct aat gac tta gaa tat gaa        624
Asn Leu Lys Ala Glu Lys Gly Gln Tyr Ser Asn Asp Leu Glu Tyr Glu
            195                     200                     205 ata gat aga gct aga tat gct gaa ata aaa aaa atg gta aaa cga ata        672
Ile Asp Arg Ala Arg Tyr Ala Glu Ile Lys Lys Met Val Lys Arg Ile
        210                     215                     220 ttt aac tat tca acc gat ggt gta ctc aac cta tat aaa ctt ttt gtt        720
Phe Asn Tyr Ser Thr Asp Gly Val Leu Asn Leu Tyr Lys Leu Phe Val
225                     230                     235                     240 gaa gag att ata gat aag tac gct aac cct aat gga ttt gta agt tta        768
Glu Glu Ile Ile Asp Lys Tyr Ala Asn Pro Asn Gly Phe Val Ser Leu
                    245                     250                     255 ctt att cca tca tct att ctt aca gat aaa act tgt aca aaa tta aga        816
Leu Ile Pro Ser Ser Ile Leu Thr Asp Lys Thr Cys Thr Lys Leu Arg
                260                     265                     270 aca cat atg ctt gta gat agc aat atc tta tca ata aag atg ata aac        864
Thr His Met Leu Val Asp Ser Asn Ile Leu Ser Ile Lys Met Ile Asn
            275                     280                     285 gaa ggt agt gga tac att gat gct cag cag gct ttg agt gca ata tta        912
Glu Gly Ser Gly Tyr Ile Asp Ala Gln Gln Ala Leu Ser Ala Ile Leu
        290                     295                     300 att caa aaa ggt aaa agg aca gaa tct att aag gta aca aaa gat tat        960
Ile Gln Lys Gly Lys Arg Thr Glu Ser Ile Lys Val Thr Lys Asp Tyr
305                     310                     315                     320 agc aat aac cct aat cag att aca gat att aac atg gaa gac att ctt       1008
Ser Asn Asn Pro Asn Gln Ile Thr Asp Ile Asn Met Glu Asp Ile Leu
                    325                     330                     335 aat gaa aac aca gga aat gct ata ttt gct att aat aat cat gaa tat       1056
Asn Glu Asn Thr Gly Asn Ala Ile Phe Ala Ile Asn Asn His Glu Tyr
                340                     345                     350 ttc att ctt aaa cag cta aga aag ttt cct gtc gtc aaa gat tta gat       1104
Phe Ile Leu Lys Gln Leu Arg Lys Phe Pro Val Val Lys Asp Leu Asp
            355                     360                     365 ttt att att aat ctt cgt gga gaa tta gat tta aca gca aat aag gat       1152
```

```
                                                            -continued

Phe Ile Ile Asn Leu Arg Gly Glu Leu Asp Leu Thr Ala Asn Lys Asp
        370                 375                 380 tct att gta aat atc gat aca ggt tat ccg ctc tta aga gga aga aat   1200
Ser Ile Val Asn Ile Asp Thr Gly Tyr Pro Leu Leu Arg Gly Arg Asn
385                 390                 395                 400 ata ggt tat tat gag att ttg gat act tgt agt ggg gag ttt gta tcg   1248
Ile Gly Tyr Tyr Glu Ile Leu Asp Thr Cys Ser Gly Glu Phe Val Ser
                    405                 410                 415 aag gat ttt ata gaa aac agc aag aaa tca cga tat att aaa gaa aag   1296
Lys Asp Phe Ile Glu Asn Ser Lys Lys Ser Arg Tyr Ile Lys Glu Lys
                420                 425                 430 aga att gtc tgt cag caa gtt gtt aat atg aag aaa gag aga agg gta   1344
Arg Ile Val Cys Gln Gln Val Val Asn Met Lys Lys Glu Arg Arg Val
            435                 440                 445 aca ttt gct tta gta gaa gaa aat tat gtt tta gga aac tca tgc aat   1392
Thr Phe Ala Leu Val Glu Glu Asn Tyr Val Leu Gly Asn Ser Cys Asn
        450                 455                 460 ttt ata tct gta atg gat aat gat tat aac att gat tta tat gct ata   1440
Phe Ile Ser Val Met Asp Asn Asp Tyr Asn Ile Asp Leu Tyr Ala Ile
465                 470                 475                 480 ctt gga cta ttc aac act tca att att aat tgg tta ttt aag tta aca   1488
Leu Gly Leu Phe Asn Thr Ser Ile Ile Asn Trp Leu Phe Lys Leu Thr
                    485                 490                 495 agt agc aat aat cat gtt aat aac tat gag att gat tgt ttt ccc gtt   1536
Ser Ser Asn Asn His Val Asn Asn Tyr Glu Ile Asp Cys Phe Pro Val
                500                 505                 510 cca att gga tct cct tat tta aat aaa att agt aac ctg gta aaa aaa   1584
Pro Ile Gly Ser Pro Tyr Leu Asn Lys Ile Ser Asn Leu Val Lys Lys
            515                 520                 525 tat ctt agt aat aaa gac tca tcg ttg cta gaa aaa ata gag gaa tat   1632
Tyr Leu Ser Asn Lys Asp Ser Ser Leu Leu Glu Lys Ile Glu Glu Tyr
        530                 535                 540 gcg tat ata gca tat gga atc aga gaa gca aaa gag gat aat gag gat   1680
Ala Tyr Ile Ala Tyr Gly Ile Arg Glu Ala Lys Glu Asp Asn Glu Asp
545                 550                 555                 560 aaa gat gat ata gct aat cta aaa gaa act aac gat att ata aaa aaa   1728
Lys Asp Asp Ile Ala Asn Leu Lys Glu Thr Asn Asp Ile Ile Lys Lys
                    565                 570                 575 tat tat tca gca ata aaa cat gtt cta cca agt ata aca ctg gaa gat   1776
Tyr Tyr Ser Ala Ile Lys His Val Leu Pro Ser Ile Thr Leu Glu Asp
                580                 585                 590 tca gtc agt atc ctt gag ggg caa tct tca ata gaa tcc ttt ata ctg   1824
Ser Val Ser Ile Leu Glu Gly Gln Ser Ser Ile Glu Ser Phe Ile Leu
            595                 600                 605 caa tct gga gtt gaa tta gat aaa tac aca cgt aat ata gtt ttg gga   1872
Gln Ser Gly Val Glu Leu Asp Lys Tyr Thr Arg Asn Ile Val Leu Gly
        610                 615                 620 att act gat aaa tat atg aaa att aaa aaa gga gaa ata ctt aat cat   1920
Ile Thr Asp Lys Tyr Met Lys Ile Lys Lys Gly Glu Ile Leu Asn His
625                 630                 635                 640 act act ttc aaa tta agt gac tta gat ttg gaa atg ata cgc tct gtt   1968
Thr Thr Phe Lys Leu Ser Asp Leu Asp Leu Glu Met Ile Arg Ser Val
                    645                 650                 655 cca ccc gga ggc aac tgg aag gac ata cca att gaa acg gta aaa aaa   2016
Pro Pro Gly Gly Asn Trp Lys Asp Ile Pro Ile Glu Thr Val Lys Lys
                660                 665                 670 ttt aag aga tta atg aga att aca gaa aca ggt ggg cga aca aca tta   2064
Phe Lys Arg Leu Met Arg Ile Thr Glu Thr Gly Gly Arg Thr Thr Leu
            675                 680                 685
```

-continued

| | | |
|---|---|---|
| tat ggt cga att gac tat gat aag cca agt tac acg att acg act tat<br>Tyr Gly Arg Ile Asp Tyr Asp Lys Pro Ser Tyr Thr Ile Thr Thr Tyr<br>690               695                 700 | | 2112 |
| ttt aat agg cct gga aat gga acc tat gtg cat cct gtt cat gat aga<br>Phe Asn Arg Pro Gly Asn Gly Thr Tyr Val His Pro Val His Asp Arg<br>705               710               715             720 | | 2160 |
| gtt ctt tct gtt agg gag gct gca cga ttc caa tgt ttt aag gat gat<br>Val Leu Ser Val Arg Glu Ala Ala Arg Phe Gln Cys Phe Lys Asp Asp<br>             725               730               735 | | 2208 |
| tat tat ttt tat gga aac aag aca caa atg ctt aaa cag gtt gga aat<br>Tyr Tyr Phe Tyr Gly Asn Lys Thr Gln Met Leu Lys Gln Val Gly Asn<br>       740              745               750 | | 2256 |
| gct gtg cca aca att cta gct tat caa att gca aag aag ata gtt gat<br>Ala Val Pro Thr Ile Leu Ala Tyr Gln Ile Ala Lys Lys Ile Val Asp<br>755               760               765 | | 2304 |
| aaa aca ggt tgt aga aag tca ata gat ctc ttc tgt ggg gca ggt gga<br>Lys Thr Gly Cys Arg Lys Ser Ile Asp Leu Phe Cys Gly Ala Gly Gly<br>   770              775              780 | | 2352 |
| tta act gca gga ttt aaa gag gct gga att caa tca gtt tta tgt aac<br>Leu Thr Ala Gly Phe Lys Glu Ala Gly Ile Gln Ser Val Leu Cys Asn<br>785               790              795             800 | | 2400 |
| gat atc gaa gaa agt gca tgt ata act ttg aaa att aat aac cct gag<br>Asp Ile Glu Glu Ser Ala Cys Ile Thr Leu Lys Ile Asn Asn Pro Glu<br>             805               810               815 | | 2448 |
| att aaa gtt tta tgt ggt gat att tct caa cat gaa aca aag gag cat<br>Ile Lys Val Leu Cys Gly Asp Ile Ser Gln His Glu Thr Lys Glu His<br>       820              825               830 | | 2496 |
| att gtt aat gtt gca ata aat gaa gat gtt gat att att tgt gga ggt<br>Ile Val Asn Val Ala Ile Asn Glu Asp Val Asp Ile Ile Cys Gly Gly<br>835               840               845 | | 2544 |
| cca cct tgt caa ggc ttt tca atg gcg gga ttg aga tta aca gat gac<br>Pro Pro Cys Gln Gly Phe Ser Met Ala Gly Leu Arg Leu Thr Asp Asp<br>   850              855              860 | | 2592 |
| cca aga aat cag ctt ttt aag gaa ttc att gaa ata gta agt cga gta<br>Pro Arg Asn Gln Leu Phe Lys Glu Phe Ile Glu Ile Val Ser Arg Val<br>865               870              875             880 | | 2640 |
| aag cct aaa gta att gta ttt gaa aat gtt gaa ggg att ctt agt ttt<br>Lys Pro Lys Val Ile Val Phe Glu Asn Val Glu Gly Ile Leu Ser Phe<br>             885               890               895 | | 2688 |
| cag agt gga aag gta tat cgt gcg ata tta gag atg ttt tca gaa ata<br>Gln Ser Gly Lys Val Tyr Arg Ala Ile Leu Glu Met Phe Ser Glu Ile<br>       900              905               910 | | 2736 |
| gga tat ttt act gaa gga cga act tta atg tca agc gac tat gcc gtt<br>Gly Tyr Phe Thr Glu Gly Arg Thr Leu Met Ser Ser Asp Tyr Ala Val<br>915               920               925 | | 2784 |
| cct caa aaa cga aag aga gtt ttt att atc tgt act cgt gat gat atg<br>Pro Gln Lys Arg Lys Arg Val Phe Ile Ile Cys Thr Arg Asp Asp Met<br>   930              935              940 | | 2832 |
| gac gta aaa ccg gca gat tta ttt cca act cct att aca gaa gag ccc<br>Asp Val Lys Pro Ala Asp Leu Phe Pro Thr Pro Ile Thr Glu Glu Pro<br>945               950              955             960 | | 2880 |
| gaa tgt caa att aca gcc agg gat act atc aaa gat tta gaa aac atc<br>Glu Cys Gln Ile Thr Ala Arg Asp Thr Ile Lys Asp Leu Glu Asn Ile<br>             965               970               975 | | 2928 |
| cag tgt gat gaa aaa gct tgt tat gtt aaa gtg gaa cat gaa tct gat<br>Gln Cys Asp Glu Lys Ala Cys Tyr Val Lys Val Glu His Glu Ser Asp<br>       980              985               990 | | 2976 |
| atc ctg aag gtt ttt aaa ggg aaa atg acg tac caa gaa ata tat tag<br>Ile Leu Lys Val Phe Lys Gly Lys Met Thr Tyr Gln Glu Ile Tyr<br>995               1000              1005 | | 3024 |

<210> SEQ ID NO 9
<211> LENGTH: 1007
<212> TYPE: PRT
<213> ORGANISM: Bacillus stearothermophilus A664

<400> SEQUENCE: 9

```
Met Asn Gly Gly Ala Cys Val Lys Glu Asn Thr Glu Ile Asn Ile Asp
  1               5                  10                  15

Ile Lys Lys Ala Ala Leu Trp Asp Thr Ile Arg Asn Lys Ser Gln Phe
                 20                  25                  30

Leu Glu Thr Gln Met Asp Pro Leu Glu Arg Lys Arg Thr Gly Ser Tyr
             35                  40                  45

Phe Thr Ala Leu Glu Leu Thr Asp Val Met Met Gln Glu Leu Val Ser
 50                  55                  60

Tyr Ile Leu Lys Ser Asp Lys Asp Ile Thr Glu Leu Lys Phe Leu Glu
 65                  70                  75                  80

Pro Cys Val Gly Thr Gly Asn Phe Val Phe Ser Tyr Leu Lys Glu Ile
                 85                  90                  95

Ser Lys Leu Gln Leu His Lys Glu Gln Ile Glu Thr Leu Ile Asn Asn
            100                 105                 110

Ile Tyr Val Ala Asp Ile Asn Gln Thr Ala Leu Leu Glu Tyr Lys Lys
            115                 120                 125

Leu Leu Ser Lys Phe Ala Lys Leu Tyr Phe Asp Ile Asp Leu Ser Glu
130                 135                 140

Glu Tyr Phe Asn Ser His Ile Gly Ser Ala Leu Leu Ile Asp Val Ala
145                 150                 155                 160

Ala Glu Gln Pro Glu Tyr Ile Lys Ile Thr Asp Val Phe Pro Asp Glu
                165                 170                 175

Val Val Lys Glu Gly Phe Asp Ile Val Val Thr Asn Pro Pro Tyr Lys
            180                 185                 190

Asn Leu Lys Ala Glu Lys Gly Gln Tyr Ser Asn Asp Leu Glu Tyr Glu
            195                 200                 205

Ile Asp Arg Ala Arg Tyr Ala Glu Ile Lys Lys Met Val Lys Arg Ile
210                 215                 220

Phe Asn Tyr Ser Thr Asp Gly Val Leu Asn Leu Tyr Lys Leu Phe Val
225                 230                 235                 240

Glu Glu Ile Ile Asp Lys Tyr Ala Asn Pro Asn Gly Phe Val Ser Leu
                245                 250                 255

Leu Ile Pro Ser Ser Ile Leu Thr Asp Lys Thr Cys Thr Lys Leu Arg
            260                 265                 270

Thr His Met Leu Val Asp Ser Asn Ile Leu Ser Ile Lys Met Ile Asn
            275                 280                 285

Glu Gly Ser Gly Tyr Ile Asp Ala Gln Gln Ala Leu Ser Ala Ile Leu
290                 295                 300

Ile Gln Lys Gly Lys Arg Thr Glu Ser Ile Lys Val Thr Lys Asp Tyr
305                 310                 315                 320

Ser Asn Asn Pro Asn Gln Ile Thr Asp Ile Asn Met Glu Asp Ile Leu
                325                 330                 335

Asn Glu Asn Thr Gly Asn Ala Ile Phe Ala Ile Asn Asn His Glu Tyr
            340                 345                 350

Phe Ile Leu Lys Gln Leu Arg Lys Phe Pro Val Val Lys Asp Leu Asp
            355                 360                 365

Phe Ile Ile Asn Leu Arg Gly Glu Leu Asp Leu Thr Ala Asn Lys Asp
```

-continued

```
            370                 375                 380
Ser Ile Val Asn Ile Asp Thr Gly Tyr Pro Leu Leu Arg Gly Arg Asn
385                 390                 395                 400
Ile Gly Tyr Tyr Glu Ile Leu Asp Thr Cys Ser Gly Glu Phe Val Ser
                    405                 410                 415
Lys Asp Phe Ile Glu Asn Ser Lys Lys Ser Arg Tyr Ile Lys Glu Lys
                420                 425                 430
Arg Ile Val Cys Gln Gln Val Val Asn Met Lys Lys Glu Arg Arg Val
            435                 440                 445
Thr Phe Ala Leu Val Glu Glu Asn Tyr Val Leu Gly Asn Ser Cys Asn
        450                 455                 460
Phe Ile Ser Val Met Asp Asn Asp Tyr Asn Ile Asp Leu Tyr Ala Ile
465                 470                 475                 480
Leu Gly Leu Phe Asn Thr Ser Ile Ile Asn Trp Leu Phe Lys Leu Thr
                    485                 490                 495
Ser Ser Asn Asn His Val Asn Asn Tyr Glu Ile Asp Cys Phe Pro Val
                500                 505                 510
Pro Ile Gly Ser Pro Tyr Leu Asn Lys Ile Ser Asn Leu Val Lys Lys
            515                 520                 525
Tyr Leu Ser Asn Lys Asp Ser Ser Leu Leu Glu Lys Ile Glu Glu Tyr
530                 535                 540
Ala Tyr Ile Ala Tyr Gly Ile Arg Glu Ala Lys Glu Asp Asn Glu Asp
545                 550                 555                 560
Lys Asp Asp Ile Ala Asn Leu Lys Glu Thr Asn Asp Ile Ile Lys Lys
                    565                 570                 575
Tyr Tyr Ser Ala Ile Lys His Val Leu Pro Ser Ile Thr Leu Glu Asp
                580                 585                 590
Ser Val Ser Ile Leu Glu Gly Gln Ser Ser Ile Glu Ser Phe Ile Leu
            595                 600                 605
Gln Ser Gly Val Glu Leu Asp Lys Tyr Thr Arg Asn Ile Val Leu Gly
        610                 615                 620
Ile Thr Asp Lys Tyr Met Lys Ile Lys Lys Gly Glu Ile Leu Asn His
625                 630                 635                 640
Thr Thr Phe Lys Leu Ser Asp Leu Asp Leu Glu Met Ile Arg Ser Val
                    645                 650                 655
Pro Pro Gly Gly Asn Trp Lys Asp Ile Pro Ile Glu Thr Val Lys Lys
                660                 665                 670
Phe Lys Arg Leu Met Arg Ile Thr Glu Thr Gly Gly Arg Thr Thr Leu
            675                 680                 685
Tyr Gly Arg Ile Asp Tyr Asp Lys Pro Ser Tyr Thr Ile Thr Thr Tyr
        690                 695                 700
Phe Asn Arg Pro Gly Asn Gly Thr Tyr Val His Pro Val His Asp Arg
705                 710                 715                 720
Val Leu Ser Val Arg Glu Ala Ala Arg Phe Gln Cys Phe Lys Asp Asp
                    725                 730                 735
Tyr Tyr Phe Tyr Gly Asn Lys Thr Gln Met Leu Lys Gln Val Gly Asn
                740                 745                 750
Ala Val Pro Thr Ile Leu Ala Tyr Gln Ile Ala Lys Lys Ile Val Asp
            755                 760                 765
Lys Thr Gly Cys Arg Lys Ser Ile Asp Leu Phe Cys Gly Ala Gly Gly
        770                 775                 780
Leu Thr Ala Gly Phe Lys Glu Ala Gly Ile Gln Ser Val Leu Cys Asn
785                 790                 795                 800
```

```
Asp Ile Glu Glu Ser Ala Cys Ile Thr Leu Lys Ile Asn Asn Pro Glu
                805                 810                 815

Ile Lys Val Leu Cys Gly Asp Ile Ser Gln His Glu Thr Lys Glu His
            820                 825                 830

Ile Val Asn Val Ala Ile Asn Glu Asp Val Asp Ile Ile Cys Gly Gly
                835                 840                 845

Pro Pro Cys Gln Gly Phe Ser Met Ala Gly Leu Arg Leu Thr Asp Asp
        850                 855                 860

Pro Arg Asn Gln Leu Phe Lys Glu Phe Ile Glu Ile Val Ser Arg Val
865                 870                 875                 880

Lys Pro Lys Val Ile Val Phe Glu Asn Val Glu Gly Ile Leu Ser Phe
                885                 890                 895

Gln Ser Gly Lys Val Tyr Arg Ala Ile Leu Glu Met Phe Ser Glu Ile
            900                 905                 910

Gly Tyr Phe Thr Glu Gly Arg Thr Leu Met Ser Ser Asp Tyr Ala Val
                915                 920                 925

Pro Gln Lys Arg Lys Arg Val Phe Ile Ile Cys Thr Arg Asp Asp Met
        930                 935                 940

Asp Val Lys Pro Ala Asp Leu Phe Pro Thr Pro Ile Thr Glu Glu Pro
945                 950                 955                 960

Glu Cys Gln Ile Thr Ala Arg Asp Thr Ile Lys Asp Leu Glu Asn Ile
                965                 970                 975

Gln Cys Asp Glu Lys Ala Cys Tyr Val Lys Val Glu His Glu Ser Asp
            980                 985                 990

Ile Leu Lys Val Phe Lys Gly Lys Met Thr Tyr Gln Glu Ile Tyr
                995                1000                1005

<210> SEQ ID NO 10
<211> LENGTH: 1398
<212> TYPE: DNA
<213> ORGANISM: Bacillus stearothermophilus A664
<220> FEATURE:
<221> NAME/KEY: CDS
<222> LOCATION: (1)..(1398)

<400> SEQUENCE: 10 atg gca aga gaa gaa aga gaa tgg cat cct aaa ttt att gaa tat atg        48
Met Ala Arg Glu Glu Arg Glu Trp His Pro Lys Phe Ile Glu Tyr Met
  1               5                  10                  15 gat ttc att att caa cat cca aat tac aaa ggt tta cca ata act aaa        96
Asp Phe Ile Ile Gln His Pro Asn Tyr Lys Gly Leu Pro Ile Thr Lys
                 20                  25                  30 aaa tct gat gga tct tgg tct tgg ttt ggt aca aag aaa aca caa att      144
Lys Ser Asp Gly Ser Trp Ser Trp Phe Gly Thr Lys Lys Thr Gln Ile
             35                  40                  45 gga aaa gca agg ata gct tgg tgt gaa aat aaa gct aaa gaa tta gga      192
Gly Lys Ala Arg Ile Ala Trp Cys Glu Asn Lys Ala Lys Glu Leu Gly
         50                  55                  60 ttt cca att gag cca ggc gtt tat gcg aat gtt atg cgt gag att cat      240
Phe Pro Ile Glu Pro Gly Val Tyr Ala Asn Val Met Arg Glu Ile His
 65                  70                  75                  80 cca acc aaa tgg aaa gta tgt caa acc tgt ggc cat tca atg tca att      288
Pro Thr Lys Trp Lys Val Cys Gln Thr Cys Gly His Ser Met Ser Ile
                 85                  90                  95 tat tat cac tat cca agt gct aat ttt ctt aag gct cta aaa aaa gag      336
Tyr Tyr His Tyr Pro Ser Ala Asn Phe Leu Lys Ala Leu Lys Lys Glu
                100                 105                 110
```

-continued

| | | |
|---|---|---|
| ttc ggt gtt gaa tat act gaa gtt gac cac atc gcc gac att tgg gat<br>Phe Gly Val Glu Tyr Thr Glu Val Asp His Ile Ala Asp Ile Trp Asp<br>115                     120                   125 | 384 |
| gat ttg ctt agc cgg ggg ttt tca aac aat aaa ata gct tca ttt ctt<br>Asp Leu Leu Ser Arg Gly Phe Ser Asn Asn Lys Ile Ala Ser Phe Leu<br>130                     135                   140 | 432 |
| ata aaa aag ggt gaa tta gat tta aac gct aaa acc tca agt aaa gat<br>Ile Lys Lys Gly Glu Leu Asp Leu Asn Ala Lys Thr Ser Ser Lys Asp<br>145                   150                   155                   160 | 480 |
| gaa gtt att tat gaa ctt gaa tca gtt tgt aga aac aaa ggg aaa aaa<br>Glu Val Ile Tyr Glu Leu Glu Ser Val Cys Arg Asn Lys Gly Lys Lys<br>                165                   170                   175 | 528 |
| ata ttg agc cct gga gcc atg tca aac ttt cca gat cga ttt gat gga<br>Ile Leu Ser Pro Gly Ala Met Ser Asn Phe Pro Asp Arg Phe Asp Gly<br>180                     185                   190 | 576 |
| ttc cat acc tat aac cgt tgc tgc aga gca tcg caa gat aag gga cgt<br>Phe His Thr Tyr Asn Arg Cys Cys Arg Ala Ser Gln Asp Lys Gly Arg<br>                195                   200                   205 | 624 |
| tca aaa gaa aac cta aaa tcg tat aca aaa gat aga cgt gca tat gaa<br>Ser Lys Glu Asn Leu Lys Ser Tyr Thr Lys Asp Arg Arg Ala Tyr Glu<br>210                     215                   220 | 672 |
| tat tgg agc gat gga aat att cat gcg gcc aac caa ttt atg ggg agc<br>Tyr Trp Ser Asp Gly Asn Ile His Ala Ala Asn Gln Phe Met Gly Ser<br>225                     230                   235                   240 | 720 |
| cca ttc ttt aat aat att tca gct gat cat att ggt cct att tca tta<br>Pro Phe Phe Asn Asn Ile Ser Ala Asp His Ile Gly Pro Ile Ser Leu<br>                245                   250                   255 | 768 |
| ggg ttt gta cat gat cca aga tat tta caa ccc atg agt ggc ggt gat<br>Gly Phe Val His Asp Pro Arg Tyr Leu Gln Pro Met Ser Gly Gly Asp<br>260                     265                   270 | 816 |
| aac tcc tct aaa aga gac cgc tta cag ttg gat gat att gaa aaa att<br>Asn Ser Ser Lys Arg Asp Arg Leu Gln Leu Asp Asp Ile Glu Lys Ile<br>                275                   280                   285 | 864 |
| att gaa act gaa aaa cgc aca aat gtt tat cct atg tca tgg tac tca<br>Ile Glu Thr Glu Lys Arg Thr Asn Val Tyr Pro Met Ser Trp Tyr Ser<br>290                     295                   300 | 912 |
| aaa tta atc tgg gaa tac ata aag aaa aat tac tct act cat aag agt<br>Lys Leu Ile Trp Glu Tyr Ile Lys Lys Asn Tyr Ser Thr His Lys Ser<br>305                     310                   315                   320 | 960 |
| tta att tct gga gtt tac cga gat gct tta aag cag aat atg tct aat<br>Leu Ile Ser Gly Val Tyr Arg Asp Ala Leu Lys Gln Asn Met Ser Asn<br>                325                   330                   335 | 1008 |
| ttt atg tat ata ttg tgg tat att ctt gag cac tgt aac caa gat ggt<br>Phe Met Tyr Ile Leu Trp Tyr Ile Leu Glu His Cys Asn Gln Asp Gly<br>340                     345                   350 | 1056 |
| gag cat ttt tta gaa gaa gct cta tta aag ccc aat tat gat tat ttt<br>Glu His Phe Leu Glu Glu Ala Leu Leu Lys Pro Asn Tyr Asp Tyr Phe<br>                355                   360                   365 | 1104 |
| caa tac tca tat aca ttt aat gaa tta gga gaa att gtg agc ata aac<br>Gln Tyr Ser Tyr Thr Phe Asn Glu Leu Gly Glu Ile Val Ser Ile Asn<br>370                     375                   380 | 1152 |
| cca cgt cac ttt act gat aga aat cag tat gaa acc gaa aga tac aaa<br>Pro Arg His Phe Thr Asp Arg Asn Gln Tyr Glu Thr Glu Arg Tyr Lys<br>385                     390                   395                   400 | 1200 |
| cgt ata gct ttt gag tca gtt tat gat tat aat gaa aaa gaa aat aga<br>Arg Ile Ala Phe Glu Ser Val Tyr Asp Tyr Asn Glu Lys Glu Asn Arg<br>                405                   410                   415 | 1248 |
| aat ata aaa gca aac ctc ata gat aat gag caa aga atg tta aac aaa<br>Asn Ile Lys Ala Asn Leu Ile Asp Asn Glu Gln Arg Met Leu Asn Lys<br>420                     425                   430 | 1296 |

```
ttg tgc cag gaa att tca tct ggg gtt cct gtt gag cag tgc aaa aaa    1344
Leu Cys Gln Glu Ile Ser Ser Gly Val Pro Val Glu Gln Cys Lys Lys
        435                 440                 445 ctt cta ata gaa tta atg gaa gta att caa aaa aga att ata tca aca    1392
Leu Leu Ile Glu Leu Met Glu Val Ile Gln Lys Arg Ile Ile Ser Thr
450                 455                 460 tta taa                                                            1398
Leu
465

<210> SEQ ID NO 11
<211> LENGTH: 465
<212> TYPE: PRT
<213> ORGANISM: Bacillus stearothermophilus A664

<400> SEQUENCE: 11

Met Ala Arg Glu Glu Arg Glu Trp His Pro Lys Phe Ile Glu Tyr Met
 1               5                  10                  15

Asp Phe Ile Ile Gln His Pro Asn Tyr Lys Gly Leu Pro Ile Thr Lys
            20                  25                  30

Lys Ser Asp Gly Ser Trp Ser Trp Phe Gly Thr Lys Lys Thr Gln Ile
        35                  40                  45

Gly Lys Ala Arg Ile Ala Trp Cys Glu Asn Lys Ala Lys Glu Leu Gly
    50                  55                  60

Phe Pro Ile Glu Pro Gly Val Tyr Ala Asn Val Met Arg Glu Ile His
65                  70                  75                  80

Pro Thr Lys Trp Lys Val Cys Gln Thr Cys Gly His Ser Met Ser Ile
                85                  90                  95

Tyr Tyr His Tyr Pro Ser Ala Asn Phe Leu Lys Ala Leu Lys Lys Glu
            100                 105                 110

Phe Gly Val Glu Tyr Thr Glu Val Asp His Ile Ala Asp Ile Trp Asp
        115                 120                 125

Asp Leu Leu Ser Arg Gly Phe Ser Asn Asn Lys Ile Ala Ser Phe Leu
    130                 135                 140

Ile Lys Lys Gly Glu Leu Asp Leu Asn Ala Lys Thr Ser Ser Lys Asp
145                 150                 155                 160

Glu Val Ile Tyr Glu Leu Glu Ser Val Cys Arg Asn Lys Gly Lys Lys
                165                 170                 175

Ile Leu Ser Pro Gly Ala Met Ser Asn Phe Pro Asp Arg Phe Asp Gly
            180                 185                 190

Phe His Thr Tyr Asn Arg Cys Cys Arg Ala Ser Gln Asp Lys Gly Arg
        195                 200                 205

Ser Lys Glu Asn Leu Lys Ser Tyr Thr Lys Asp Arg Arg Ala Tyr Glu
    210                 215                 220

Tyr Trp Ser Asp Gly Asn Ile His Ala Ala Asn Gln Phe Met Gly Ser
225                 230                 235                 240

Pro Phe Phe Asn Asn Ile Ser Ala Asp His Ile Gly Pro Ile Ser Leu
                245                 250                 255

Gly Phe Val His Asp Pro Arg Tyr Leu Gln Pro Met Ser Gly Gly Asp
            260                 265                 270

Asn Ser Ser Lys Arg Asp Arg Leu Gln Leu Asp Asp Ile Glu Lys Ile
        275                 280                 285

Ile Glu Thr Glu Lys Arg Thr Asn Val Tyr Pro Met Ser Trp Tyr Ser
    290                 295                 300

Lys Leu Ile Trp Glu Tyr Ile Lys Lys Asn Tyr Ser Thr His Lys Ser
```

|    |     |     |     |     |     | 305 |     |     |     |     |     | 310 |     |     |     |     |     | 315 |     |     |     |     |     | 320 |
|----|-----|-----|-----|-----|-----|-----|-----|-----|-----|-----|-----|-----|-----|-----|-----|-----|-----|-----|-----|-----|-----|-----|-----|-----|

Leu Ile Ser Gly Val Tyr Arg Asp Ala Leu Lys Gln Asn Met Ser Asn
            325                 330                 335

Phe Met Tyr Ile Leu Trp Tyr Ile Leu Glu His Cys Asn Gln Asp Gly
            340                 345                 350

Glu His Phe Leu Glu Glu Ala Leu Leu Lys Pro Asn Tyr Asp Tyr Phe
            355                 360                 365

Gln Tyr Ser Tyr Thr Phe Asn Glu Leu Gly Glu Ile Val Ser Ile Asn
    370                 375                 380

Pro Arg His Phe Thr Asp Arg Asn Gln Tyr Glu Thr Glu Arg Tyr Lys
385                 390                 395                 400

Arg Ile Ala Phe Glu Ser Val Tyr Asp Tyr Asn Glu Lys Glu Asn Arg
                405                 410                 415

Asn Ile Lys Ala Asn Leu Ile Asp Asn Glu Gln Arg Met Leu Asn Lys
            420                 425                 430

Leu Cys Gln Glu Ile Ser Ser Gly Val Pro Val Glu Gln Cys Lys Lys
        435                 440                 445

Leu Leu Ile Glu Leu Met Glu Val Ile Gln Lys Arg Ile Ile Ser Thr
    450                 455                 460

Leu
465

<210> SEQ ID NO 12
<211> LENGTH: 54
<212> TYPE: DNA
<213> ORGANISM: Bacillus stearothermophilus A664

<400> SEQUENCE: 12
ggtggtgcta gcggaggtaa ataaatgaaa gaaaacacag aaattaatat agat       54

<210> SEQ ID NO 13
<211> LENGTH: 39
<212> TYPE: DNA
<213> ORGANISM: Bacillus stearothermophilus A664

<400> SEQUENCE: 13
ggtggtgcat gcctaatata tttcttggta cgtcattt                          39

<210> SEQ ID NO 14
<211> LENGTH: 24
<212> TYPE: DNA
<213> ORGANISM: Escherichia coli

<400> SEQUENCE: 14
ttcaaaaaag aattatatca acat                                         24

<210> SEQ ID NO 15
<211> LENGTH: 24
<212> TYPE: DNA
<213> ORGANISM: Escherichia coli

<400> SEQUENCE: 15
ttacttccat taattctatt agaa                                         24

<210> SEQ ID NO 16
<211> LENGTH: 24
<212> TYPE: DNA
<213> ORGANISM: Unknown
<220> FEATURE:
<223> OTHER INFORMATION: Description of Unknown Organism: Inverse PCR -continued

```
    Primers

<400> SEQUENCE: 16
ttgacatact ttccatttgg ttgg                                            24

<210> SEQ ID NO 17
<211> LENGTH: 24
<212> TYPE: DNA
<213> ORGANISM: Unknown
<220> FEATURE:
<223> OTHER INFORMATION: Description of Unknown Organism: Inverse PCR
      Primers

<400> SEQUENCE: 17
ggccattcaa tgtcaattta ttat                                            24

<210> SEQ ID NO 18
<211> LENGTH: 6
<212> TYPE: DNA
<213> ORGANISM: Bacillus amyloliquefaciens
<220> FEATURE:
<223> OTHER INFORMATION: Description of Unknown Organism: Inverse PCR
      Primers

<400> SEQUENCE: 18 ggatcc                                                                 6

<210> SEQ ID NO 19
<211> LENGTH: 51
<212> TYPE: DNA
<213> ORGANISM: Bacillus stearothermophilus A664
<220> FEATURE:
<223> OTHER INFORMATION: Description of Unknown Organism: Inverse PCR
      Primers

<400> SEQUENCE: 19
ggtggtggat ccggaggtaa ataaatggca agagaagaaa gagaatggca t              51

<210> SEQ ID NO 20
<211> LENGTH: 39
<212> TYPE: DNA
<213> ORGANISM: Bacillus stearothermophilus A664

<400> SEQUENCE: 20
ggtggtggat ccttataatg ttgatataat tcttttttg                            39
```

US 6,596,524 B2

METHOD FOR CLONING AND EXPRESSION OF BSMAI RESTRICTION ENDONUCLEASE AND BSMAI METHYLASE IN E. COLI

BACKGROUND OF THE INVENTION

The present invention relates to recombinant DNA encoding the BsmAI restriction endonuclease (endonuclease) as well as BsmAI methyltransferase (methylase), as well as expression of BsmAI endonuclease and methylase in E. coli cells containing the recombinant DNA.

BsmAI endonuclease is found in the strain of Bacillus stearothermophilus A664 (New England Biolabs' strain collection #481). It recognizes the double-stranded DNA sequence 5' GTCTC 3' N1/N5 (SEQ ID NO:1) and cleaves downstream sequence at N1 (top strand) and N5 (bottom strand) to generate a 4-base 5' overhang (/ indicates the cleavage of phosphodiester bond). BsmAI methylase (M.BsmAI) is also found in the same strain.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') on DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are discovered. Thus, the species Deinococcus radiophilus for example, produces three different restriction endonucleases, named DraI, DraII and DraIII. These enzymes recognize and cleave the sequences 5' TTT/AAA 3' (SEQ ID NO:2), 5' PuG/GNCCPy 3' (SEQ ID NO:3) and 5° CACNNN/GTG 3' (SEQ ID NO:4) respectively. Escherichia coli RY13, on the other hand, produces only one enzyme, EcoRI, which recognizes the sequence 5' G/AATTC 3' (SEQ ID NO:5).

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., Mol. Gen. Genet. 178: 717–719, (1980); HhaII: Mann et al., Gene 3: 97–112, (1978); PstI: Walder et al., Proc. Nat. Acad. Sci. 78: 1503–1507, (1981)). Since the expressions of restriction-modification systems in bacteria enable them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into E. coli cloning vectors (EcoRV: Bougueleret et al., Nucl. Acids. Res. 12: 3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne et al. Gene 202:83–88, (1997)).

A third approach is to select for active expression of methylase genes (methylase selection) (U.S. Pat. No. 5,200,333 and BsuRI: Kiss et al., Nucl. Acids. Res. 13:6403–6421, (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baldauf, Gene 21:111–119, (1983); and MspI: Walder et al., J. Biol. Chem. 258:1235–1241, (1983)).

A more recent method, the "endo-blue method", has been described for direct cloning of thermostable restriction endonuclease genes into E. coli based on the indicator strain of E. coli containing the dinD::lacZ fusion (Fomenkov et al., U.S. Pat. No. 5,498,535; Fomenkov et al., Nucl. Acids Res. 22:2399–2403, (1994)). This method utilizes the E. coli SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that sometimes positive blue clones containing a restriction endonuclease gene are difficult to culture due to the lack of the cognate methylase gene.

There are three major groups of DNA methylases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632, (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5'CCWGG3' (W=A or T) (SEQ ID NO:6) can also make the DNA resistant to PspGI restriction digestion. Another example is that CpG methylase can modify the CG dinucloetide and make the NotI site (5'GCGGCCGC3' (SEQ ID NO:7)) refractory to NotI digestion (New England Biolabs' Catalog, 2000–01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a great commercial interest to obtain bacterial strains through recombinant DNA techniques that produce large quantities of restriction enzymes. Such over-expression strains should also simplify the task of enzyme purification.

SUMMARY OF THE INVENTION

The present invention relates to a method for cloning BsmAI methylase gene from *Bacillus stearothermophilus* A664 into *E. coli* by methylase selection and inverse PCR amplification of the adjacent DNA containing BsmAI restriction endonuclease gene.

At first an ApoI partial genomic DNA library was constructed using the cloning vector PRRS (Ap$^R$). No methylase positive clones were identified following the methylase selection method. No resistant clones were found in Aat II, Bg/II, HindIII, KpnI, NdeI, PstI, SacI, SalI, SphI, and XbaI genomic DNA libraries after BsmAI challenge and retransformation with the cloning vector pUC19 (Ap$^R$). This negative result indicated that the selection was not strong enough. To increase the selection efficiency, another cloning vector pBR322 with two drug resistance markers was then used for methylase selection. In addition to two drug selection markers, there is a BsmAI site in the rop gene of pBR322. Disruption of the rop gene may further reduce the background in methylase selection.

AatII, ClaI, EcoRI, HindIII, and NdeI genomic DNA libraries were constructed using pBR322 as the cloning vector. Both Ap$^R$ and Tc$^R$ markers were used for selection following BsmAI digestion. BsmAI-resistant clones carrying BsmAI methylase gene was discovered in the NdeI DNA library. DNA sequence analysis of the insert and further inverse PCR revealed that BsmAI methylase is comprised of two fused methylases, one of them is a C5 methylase and the other is an amino-methyltransferase.

Since restriction genes are usually located in close proximity to methylase genes, inverse PCR was employed to clone the adjacent DNA surrounding the bsmAIM gene. Open reading frames (ORF) were identified on both sides of the bsmAIM gene. The downstream ORF showed strong homology to a RNA methylase in GenBank and thus it was not the BsmAI endonuclease gene. The upstream ORF did not show significant homology to any gene in Genbank and was predicted to encode the BsmAI endonuclease gene. This ORF was cloned into the expression vector pACYC-T7ter, which was derived from pACYC184, pET11, and pAII17. In order to express bsmAIR gene in *E. coli*, the bsmAIM gene (M1::M2 fusion) was first cloned in pBR322 to premodify T7 expression host ER2566. BsmAI endonuclease activity was detected in IPTG-induced cell extracts. Three clones with high BsmAI activity were sequenced and confirmed to contain the wild type sequence.

BRIEF DESCRIPTION OF THE DRAWINGS

FIG. 2. DNA sequence of BsmAI methylase gene (bsmAIM, 3024 bp) (SEQ ID NO:8) and its encoded amino acid sequence (SEQ ID NO:9).

FIG. 3. DNA sequence of BsmAI endonuclease gene (bsmAIR, 1398 bp) (SEQ ID NO:10) and its encoded amino acid sequence (SEQ ID NO:11).

DETAILED DESCRIPTION OF THE INVENTION

Figure 1:
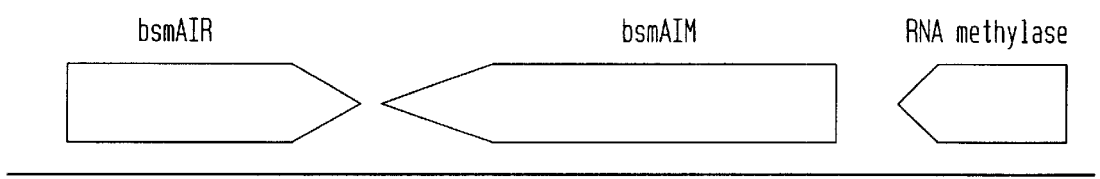
FIG. 1. Gene organization of BsmAI restriction-modification system. bsmAIR, BsmAI restriction endonuclease gene; bsmAIM, BsmAI methylase gene.
Figure 4:
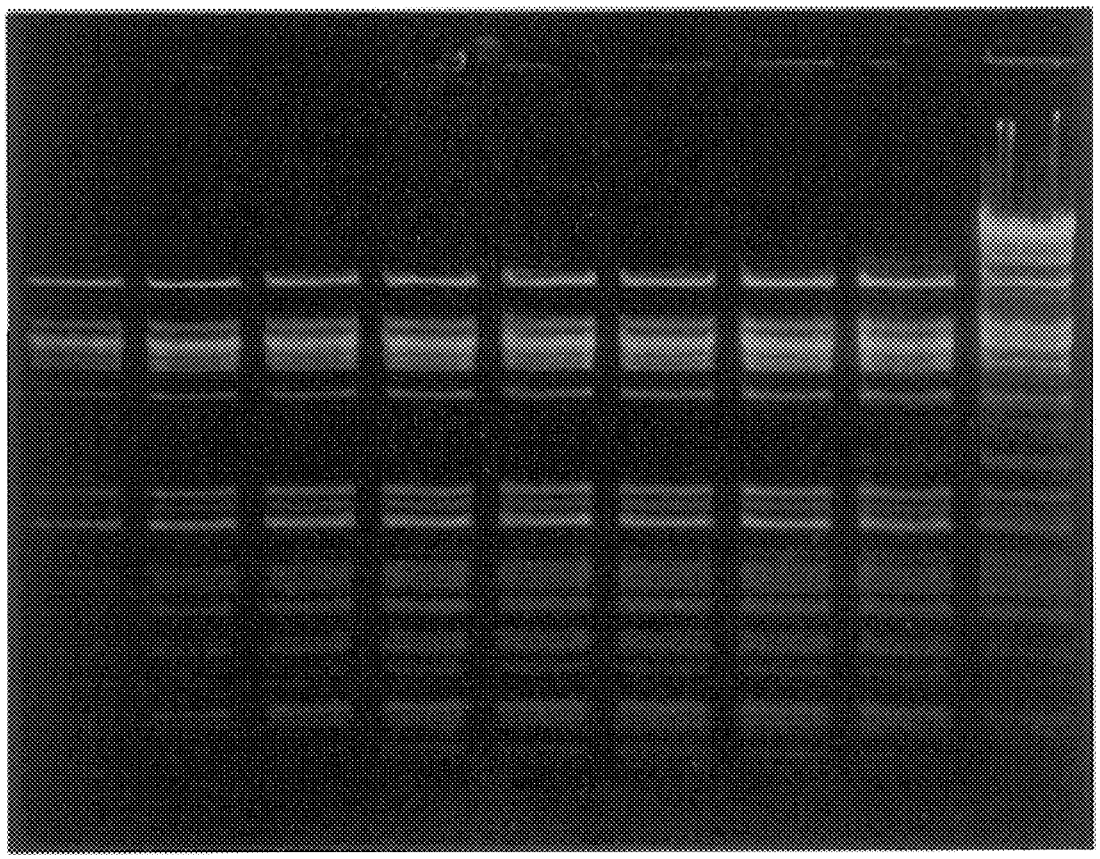
FIG. 4. Recombinant BsmAI restriction endonuclease activity in cell extract. Lane 1, Positive control, λ DNA digested with purified native BsmAI; lanes 2–9, λ DNA treated with serially diluted cell extract containing recombinant BsmAI restriction endonuclease.

The cloning of BsmAI methylase gene proved to be very difficult even though high-copy-number cloning vectors such as pRRS and pUC19 were used. BsmAI genomic DNA was partially digested with ApoI and DNA fragment between 3–10 kb was gel-purified and then ligated to EcoRI digested and CIP treated pRRS. The ligated DNA was used to transform ER2502. Plasmid DNA was prepared from amplified transformants and challenged with BsmAI. Following BsmAI digestion, the DNA mixture was transformed back into *E. coli* ER2683 cells. Transformants were screened for resistance to BsmAI digestion. Out of 54 screened no true resistant clones were identified. More genomic DNA libraries were constructed from complete digestion of genomic DNA by AatII, BglII, HindIII, KpnI, NdeI, PstI, SacI, SalI, SphI, or XbaI using cloning vector pUC19. Out of 92 clones screened there were no true BsmAI resistant clones identified. These negative results indicated that the selection was not strong enough.

To increase the genetic selection efficiency, another cloning vector pBR322 with two drug resistance markers was then used for methylase selection. In addition to two drug selection markers, there is a BsmAI site in the rop gene of pBR322. Disruption of the rop gene may further reduce the background in methylase selection. This cloning strategy proved to be successful in cloning of bsmAIM gene. AatII, ClaI, EcoRI, HindIII, and NdeI genomic DNA libraries were constructed with pBR322. Following BsmAI challenge and retransformation, 9 out of 18 clones were found to be resistant to BsmAI digestion. Sequence analysis of the insert among the resistant clones and inverse PCR products revealed that BsmAI methylase is a fusion of two methylases (amino-methyltransferase and C5 methylase).

After the BsmAI methylase gene was cloned, inverse PCR was used to obtain the adjacent DNA sequences. Inverse PCR products were obtained from BsrGI, ClaI, DdeI, DraI, EcoRV, HincII, HindIII, HinfI, MfeI, MseI, NlaIII, PstI, PvuII, RsaI, Sau96I, SspI, TaqI, and Tsp45I digested and self-ligated DNA. The inverse PCR products were sequenced directly. Open reading frames were found on the both side of the methylase gene. The downstream ORF was found to be homologous to a RNA methylase gene, so it was ruled out as the bsmAIR gene. The upstream ORF, however, has no significant homology to any gene in the Genebank. Therefore, it was predicted to encode BsmAI endonuclease. It was expressed in *E. coli* and proved to be the bsmAIR gene.

BsmAI endonuclease was expressed by a two-plasmid expression system. The bsmAIM gene was first cloned in pBR322 to premodify expression host ER2566, and the putative bsmAIR gene was cloned in a T7 vector pACYC-T7ter. BsmAI endonuclease activity was detected in the cell extract of IPTG-induced cells. The bsmAIR gene in the over-expression clone was re-confirmed to contain the wild type sequence.

The method described herein by which the bsmAIM and bsmAIR genes are preferably cloned and expressed in *E. coli* using the following steps:

1. Construction of Genomic DNA Libraries and Methylase Selection

Genomic DNA was prepared from *Bacillus stearothermophilus* A664 and digested with restriction enzymes AatII, ClaI, HindIII, EcoRI and NdeI. Genomic DNA libraries were constructed using pBR322 vector. The ligated DNA was transformed into restriction minus *E. coli* electrocompetent cell ER2502 by electroporation. Approximately 32,000 transformants were pooled and amplified overnight in 1 liter culture. Primary plasmid DNA libraries were prepared by Qiagen Maxi column method and challenged with BsmAI. Following digestion, the plasmids were transformed into ER2502. Plasmids were prepared from $Ap^R$ and $Tc^R$ survivors and screened for resistance to BsmAI digestion. The resistant clones were identified as true methylase positive clones by DNA sequencing. The entire insert was sequenced by pBR322 primers and custom-made primers. Inverse PCR was used to amplify the surrounding sequence from ApoI, BglII, EcoRI, HinfI, NlaIII, RsaI, Sau96I, TaqI, TfiI, Tsp45I digested and self-ligated template. The bsmAIM gene is 3024 bp, encoding a 1007-amino acid protein with predicted molecular mass of 115.0 kDa. This methylase is a fusion of an N6A amino-methylase and a C5 methylase.

2. Cloning of bsmAIR Gene by Inverse PCR

The Genomic DNA was digested with 4–6 bp cutting restriction enzymes such as BsrGI, ClaI, DdeI, DraI, EcoRV, HincII, HindIII, HinfI, MfeI, MseI, NlaIII, PstI, PvuII, RsaI, Sau96I, SspI, TaqI, and Tsp45I. The digested DNA was self-ligated at a low DNA concentration and then used for inverse PCR amplification of the adjacent DNA. Inverse PCR products were derived, gel-purified and sequenced. An ORF of 1398 bp was found upstream of the bsmAIM gene. This ORF was predicted to be the bsmAIR gene. Expression of this ORF confirmed the above prediction. This ORF encodes a 465-aa protein with predicted molecular mass of 54.7 kDa.

3. Cloning of bsmAIM Gene into pBR322 to Construct a Premodified Host

The bsmAIM gene was amplified from the genomic DNA by PCR using two primers. The PCR DNA was digested with NheI and SphI and ligated to pBR322. The premodified host ER2566 [pBR322-BsmAIM] was used for expression of the bsmAIR gene in *E. coli*.

4. Expression of bsmAIR Gene in T7 Expression Vector pACYC-T7ter

A BamHI fragment containing the bsmAIR gene was cloned into pACYC-T7ter expression vector. The ligated recombinant DNA was transformed into pre-modified host ER2566 [pBR322-BsmAIM]. The $Ap^R$ $Cm^R$ transformants were induced with IPTG. Recombinant BsmAI activity was detected in the supernatant of the IPTG-induced cell extract. Plasmids were extracted from those clones with high activity. After sequencing the insert, clones with wild type sequence was used for stability study and purification of BsmAI endonuclease.

5. Purification of BsmAI Endonuclease

Cell extract containing the recombinant BsmAI endonuclease was purified by heat treatment and chromatography through Heparin-Sepharose and DEAE-Sepharose columns.

The present invention is further illustrated by the following Example. This Example is provided to aid in the understanding of the invention and is not construed as a limitation thereof.

The references cited above and below are herein incorporated by reference.

EXAMPLE I

Cloning of BsmAI Restriction-modification System in *E. coli*

1. Preparation of Genomic DNA and Restriction Digestion of Genomic DNA and Construction of Genomic DNA Libraries Genomic DNA was prepared from *Bacillus stearothermophilus* A664 (New England Biolabs' collection #481) by the standard procedure consisting of the following steps:

(a) cell lysis by addition of lysozyme (2 mg/ml final), sucrose (1% final), and 50 mM Tris-HCl, pH 8.0;

(b) cell lysis by addition of 10% SDS (final concentration 0.1%);

(c) further cell lysis by addition of 1% Triton X-100 and 62 mM EDTA, 50 mM Tris-HCl, pH 8.0;

(d) phenol-$CHCl_3$ extraction of DNA 3 times (equal volume) and $CHCl_3$ extraction once;

(e) DNA dialysis in 4 liters of TE buffer, change 3 times; and (f) RNA removal by RNase A treatment and the genomic DNA was precipitated with 95% ethanol, washed with 70% ethanol, vacuum dried and resuspended in TE buffer.

Restriction enzyme ApoI was diluted by 2-fold serial dilutions. Five μg genomic DNA was digested partially with ApoI at 50° C. for 30 min. The ApoI digested genomic DNA was ligated to EcoRI digested and CIP treated pRRS vector. The ligated DNA was used to transform ER2502 electrocompetent cells by electroporation.

BsmAI genomic DNA was also completely digested with AatII, BglII, ClaI, EcoRI, HindIII, KpnI, NdeI, PstI, SacI, SalI, SphI, XbaI and DNA fragments were then ligated to pRRS, pUC19, and pBR322. The ligated DNA was used to transform ER2502 competent cells.

2. Cloning of M.BsmAI by the Methylase Selection Method

Methylase selection was performed for the ApoI partial DNA library. More than 50,000 transformants were obtained. All of the colonies were pooled and amplified in 1 liter overnight culture. Plasmid DNA was extracted by the Qiagen Maxi-prep kit. One, 2, 3 μl of library DNA (0.5–1.5 μg) was challenged with 100 u BsmAI at 55° C. for 1 hour. The challenged plasmid DNA was used for re-transformation into ER2502 and plated on Amp plates. Eighteen colonies were screened for resistance. However, none of the plasmids was resistant to BsmAI digestion.

More DNA libraries were constructed from ApoI partially digested genomic DNA and completely digested genomic DNA with AatII, BglII, HindIII, KpnI, NdeI, PstI, SacI, SalI, SphI, XbaI. One out of 54 screened (#10) showed partial resistance to BsmAI digestion. Further characterization of this clone revealed that it was a false positive. It was concluded that it was difficult to clone the BsmAI methylase gene using PRRS or pUC19.

To increase the selection efficiency, another cloning vector pBR322 with two drug resistance markers was then used for methylase selection. In addition to two drug selection markers, there is a BsmAI site in the rop gene of pBR322. Disruption of the rop gene may further reduce the background of methylase selection. This cloning strategy of using pBR322 as the cloning vector proved to be successful in cloning the bsmAIM gene.

Genomic DNA libraries were constructed from AatII, ClaI, EcoRI, HindIII, and NdeI digested DNA with pBR322 as the cloning vector. Ten μg of genomic DNA was digested with AatII, ClaI, EcoRI, HindIII, and NdeI respectively. Plasmid pBR322 was digested with AatII, ClaI, EcoRI, HindIII, or NdeI and treated with CIP. The AatII, ClaI, HindIII, EcoRI and NdeI digested genomic DNA was ligated to pBR322 with the compatible ends overnight at 16° C. The ligated DNA was dialysed in distilled water by drop dialysis and then transformed into restriction minus E. coli electro-competent cell ER2502 by electroporation. Transformants were plated on Ap (100 μg/ml) and Tc (15 μg/ml) plates. Approximately 32,000 transformants were pooled and amplified overnight in 1 liter culture. Primary plasmid DNA libraries were prepared by Qiagen Maxi column method. One tenth, 0.3, 0.5, and 0.7 μg plasmid DNA were challenged with BsmAI endonuclease at 55° C. overnight. Following digestion, the plasmids were re-transformed into ER2502. Plasmids were prepared from $Ap^R$ and $Tc^R$ survivors and screened for resistance to BsmAI restriction digestion. Nine out of 18 screened showed resistance. Two resistant clones were identified as true methylase positive clones by DNA sequencing. The inserts were sequenced with pBR322 primers and custom-ordered primers.

3. Inverse PCR Cloning/sequencing of the Adjacent DNA

Bacillus stearothermophilus A664 genomic DNA was digested with restriction enzymes with 4, 5 or 6-bp recognition sequence to identify DNA fragments that encompass bsmAIM gene and the flanking DNA. The genomic DNA was digested with ApoI, BglII, BspHI, BsrFI, BsrGI, ClaI, DdeI, DraI, EcoRI, EcoRV, HincII HinfI, MfeI, MseI, NlaIII, NspI, PstI, PvuII, RsaI, Sau96I, SspI, StuI TaqI, TfiI, Tsp45I. The genomic DNA fragments were self-ligated at a low concentration (2 μg/ml), and the ligated circles were used as the template for inverse PCR. Inverse PCR products were gel-purified and sequenced directly. The entire methylase gene was sequenced. It was found that this methylase is a fusion of two methylases (N6A methylase and C5 methylase). Among most of the C5 methylases, the conserved blocks IX and X is located at the C-terminus of the protein, followed by blocks I to VIII and the variable region. However, in BsmAI methylase blocks IX and X are located at the N-terminus of C5 methylase (blocks IX and X proceeding block I-VIII). It displays circular permutation of motifs IX and X. Such circular permutation has been found in the BssHII methylase. Based on the amino acid sequence comparison with other amino-methylases, the amino-methylase portion of the BsmAI methylase is predicted to be a γ type of N6A methylase.

DNA sequences adjacent to BsmAI methylase gene were obtained by inverse PCR and DNA sequencing. Five rounds of inverse PCR were performed to obtain about 1,453 bp of downstream sequence. Comparison of the downstream sequence with known genes in Genbank indicated that one partial ORF has homology with RNA methylase. It was concluded that the bsmAIR gene might be located upstream of the methylase gene.

4. Cloning of bsmAIM Gene into pBR322 to Construct a Premodified Host

Two primers were synthesized with the following sequence:

5' GGTGGTGCTAGCGGAGGTAAATAAAT-GAAAGAAAACACAGAAATT AATATAGAT 3' (253-245) (SEQ ID NO:12)

5' GGTGGTGCATGCCTAATATATTTCTTGG-TACGTCATTTT 3' (253-246) (SEQ ID NO:13)

The bsmAIM gene was amplified from the genomic DNA in PCR using primers 253-245 and 253-246 under PCR condition of 95° C. 1 min, 55° C. 1 min, 72° C. 4 min for 25 cycles. The PCR DNA was purified through a Qiagen spin column and digested with NheI and SphI. The PCR fragment was purified again in low melting agarose gel and ligated to pBR322 with compatible ends. Ligated plasmid was transformed into ER2566 (T7 expression strain from NEB). The $Ap^R$ transformants were pooled and plasmid DNA prepared. The plasmid mixture was challenged with BsmAI endonuclease and retransformed back into ER2566 cells. Four out of six clones were found to have the right size insert and resistant to BsmAI digestion. The pre-modified host ER2566 [pBR322-BsmAIM] was used for expression of the bsmAIR gene in E. coli.

5. Cloning of bsmAIR Gene by Inverse PCR

Inverse PCR was used for amplification of upstream DNA. The inverse PCR products were sequenced directly to obtain new sequence. The inverse PCR primers have the following sequence:

5' TTCAAAAAAGAATTATATCAACAT 3' (232-2) (SEQ ID: 14)

5' TTACTTCCATTAATTCTATTAGAA 3' (230-166) (SEQ ID: 15)

BsmAI genomic DNA was digested with DdeI, DraI, EcoRV, HindIII, HinfI, MfeI, NlaIII, RsaI, and SspI, respectively at 37° C. for 2 h. The restricted DNA was purified by Qiagen spin column and then used for self-ligation. Two μg DNA was ligated in 500 μl volume (2 μg DNA, 50 μl 10x ligation buffer, 2000 units T4 DNA ligase, sterile distilled water to 500 μl, 16° C. overnight). The ligated DNA was heat-treated at 65° C. for 30 min to inactivate T4 DNA ligase and 20 μl DNA was used as template for inverse PCR. Inverse PCR condition was 94° C. 2 min for 1 cycle, 95° C. 1 min, 55° C. 1 min, 72° C. 1 min for 40 cycles. PCR products were found in MfeI (1 kb new sequence), RsaI (350 bp new sequence), NlaIII (400 bp new sequence), and SspI (560 bp new sequence) samples, gel-purified, and sequenced. After the entire 1.3 kb MfeI PCR fragment was sequenced, about 1 kb new sequence was obtained, but a start codon for the bsmAIR gene had not been detected in the newly derived sequence.

A second round of inverse PCR was performed in order to further extend the bsmAIR gene. The inverse PCR primers have the following sequences:

5' TTGACATACTTTCCATTTGGTTGG 3' (234-41) (SEQ ID NO:16)

5' GGCCATTCAATGTCAATTTATTAT 3' (234-42) (SEQ ID NO:17)

BsmAI genomic DNA was digested with BsrGI, ClaI, DdeI, DraI, HincII, MseI, NlaIII, PvuII, PstI, RsaI, Sau96I, SspI, TaqI, and, Tsp45I, respectively for two h at the appropriate temperatures. The restricted DNA was purified by Qiagen spin column and then use for self-ligation. Two μg DNA was ligated in 500 μl volume (2 μg DNA, 50 μl 10x ligation buffer, 2000 units T4 DNA ligase, sterile distilled water to 500 μl, 16° C. overnight). The ligated DNA was heat treated at 65° C. for 30 min to inactivate T4 DNA ligase and 20 μl circular DNA was used as template DNA for inverse PCR. Inverse PCR condition was 94° C. 2 min. for 1 cycle, 94° C. 30 sec, 50° C. 1 min, 72° C. 2 min for 30 cycles. PCR products were found in DraI (1.3 kb new sequence), MseI (200 bp new sequence), and NlaIII (450 bp new sequence) samples, gel-purified, and sequenced. An ORF of 1398 bp was found upstream of the bsmAIM gene. This ORF was predicted to be the bsmAIR gene. It encodes a 465-amino acid protein with predicted molecular mass of 54.7 kDa.

6. Expression of BsmAIR Gene in T7 Expression Vector pACYC-T7ter

To construct a stable expression clone, the bsmAIM gene was expressed from a medium-copy-number vector pBR322 and the bsmAIR gene was expressed from a low-copy-number vector pACYC-T7ter. The vector pACYC-T7ter contains a T7 promoter, $Cm^R$ gene, lacI gene, p15A replication origin, and four copies of transcription terminators upstream of T7 promoter to reduce run-off transcription from cryptic *E. coli* promoters.

BamHI restriction sites (5' GGATCC 3' (SEQ ID NO:18)) were incorporated into the forward and reverse PCR primers for amplification of bsmAIR gene by PCR. The primers have the following sequence:

5' GGTGGTGGATCCGGAGGTAAATAAATG-GCAAGAGAAGAAAGAGAA TGGCAT 3' (253-243) (SEQ ID NO:19)

5' GGTGGTGGATCCTTATAATGT-TGATATAATTCTTTTTTG 3' (253-244) (SEQ ID NO:20)

The bsmAIR gene was amplified by PCR using Vent DNA polymerase and primers 253-243 and 253-244 under conditions of 95° C. 1 min, 55° C. 1 min, 72° C. 1.5 min for 25 cycles. The PCR product was purified by Qiagen spin column and digested overnight with BamHI. After DNA purification from low-melting agarose gel, the PCR DNA was ligated to CIP-treated pACYC-T7ter with compatible ends. The ligated DNA was transformed into pre-modified host ER2566 [pBR322-BsmAIM] and selected for $Ap^R$ $Cm^R$ transformants. Individual transformants were then picked and cultured in 10 ml LB plus Ap (100 μg/ml) and Cm (33 μg/ml) and induced with IPTG (0.5 mM final) for 3 h. Forty eight cell extracts were assayed for BsmAI activity. Three clones (#12, #14, #23) were highly active and another two clones (#17, #36) had lower activity. The low activity clones were discarded due to PCR mutations. The plasmids from highly active clones were sequenced, and all three were found to contain the wild type sequence and one clone (#14) was used in subsequent large scale purification of BsmAI endonuclease protein.

7. Purification of BsmAI Endonuclease

Figure 5:
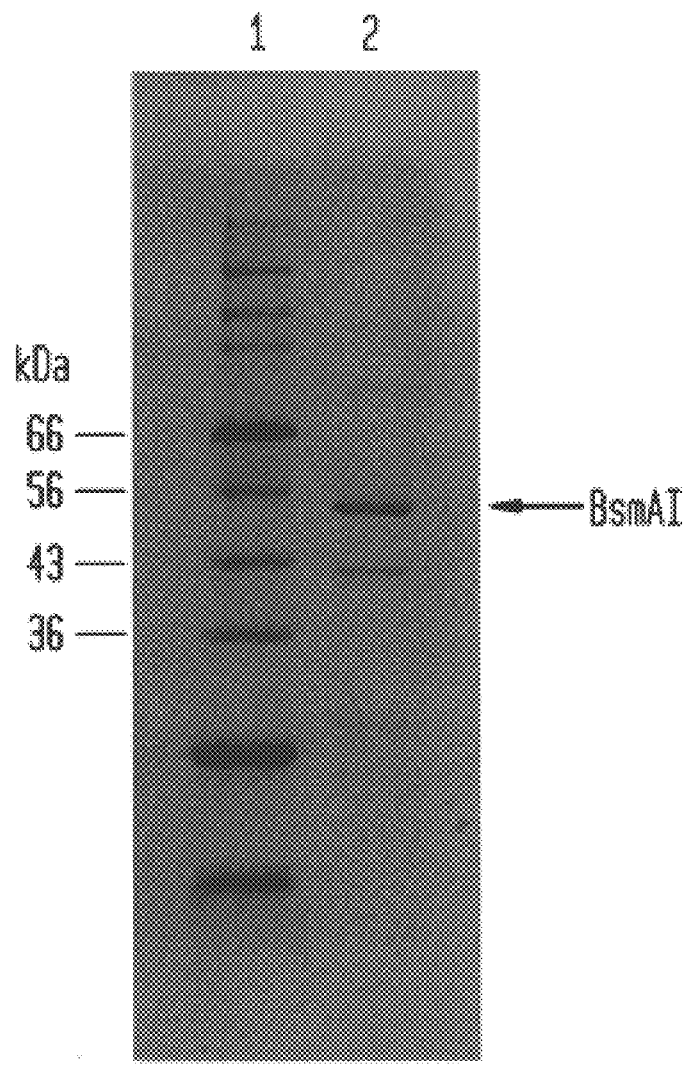
FIG. 5. Purified recombinant BsmAI restriction endonuclease protein on SDS-PAG gel. Lane 1, broad range protein molecular weight marker; lane 2, partially purified BsmAI endonuclease.

Cell extract was prepared by sonication of 4 grams of IPTG-induced cells resuspended in 20 ml sonication buffer (50 mM Tris-HCl pH 7.8, 10 mM β-mercaptoethanol). Cell debris was removed by centrifugation. The cell extract was heated at 55° C. for one hour to denature *E. coli* thermolabile proteins. Denatured proteins were removed by centrifugation. The supernatant was loaded onto a 20 ml Heparin Slepharose column. Following extensive washing with low salt buffer (20 mM Tris-HCl, pH 7.5, 50 mM NaCl, 10 mM β-mercaptoethanol, 0.1 mM EDTA), fractions were eluted with a NaCl gradient of 0.05 M–1 M. Fractions containing BsmAI endonuclease as determined by an activity assay were pooled and dialyzed overnight in DEAE-Sepharose loading buffer (20 mM Tris-HCl, pH 7.5, 50 mM NaCl, 10 mM β-mercaptoethanol, 0.1 mM EDTA). After dialysis, the protein mixture was loaded onto a DEAE Sepharose column equilibrated with the same buffer. Fractions were eluted with a 0.05 M–1 M NaCl gradient and those fractions containing purified BsmAI were pooled. The recombinant BsmAI was purified and was devoid of non-specific endo/exonuclesaes (FIG. 5). A total of 1,000,000 units of functionally purified BsmAI were obtained.

The strain ER2566 [pBR322-BsmAIM, pACYC-T7ter-BsmAIR] has been deposited under the terms and conditions of the Budapest Treaty with the American Type Culture Collection on Sep. 20, 2001 and received ATCC Accession No. PTA-3712.

What is claimed is:

1. Isolated DNA coding for the BsmAI restriction endonuclease, wherein the isolated DNA is obtainable from *Bacillus stearothermophilus* A664.

2. A recombinant DNA vector comprising a vector into which a DNA segment encoding the BsmAI restriction endonuclease gene has been inserted.

3. Isolated DNA encoding the BsmAI restriction endonuclease and BsmAI methylase, wherein the isolated DNA is obtainable from ATCC Accession No. PTA-3712.

4. A vector which comprises the isolated DNA of claim 3.

5. A host cell transformed by the vector of claims 2 or 4.

6. A method of producing recombinant BsmAI restriction endonuclease comprising culturing a host cell transformed with the vector of claims 2 or 4 under conditions suitable for expression of said endonuclease.

* * * * *